(12) United States Patent
Nonoyama et al.

(10) Patent No.: US 10,377,749 B2
(45) Date of Patent: Aug. 13, 2019

(54) PURIFICATION METHOD FOR 5-(THIAZOL-4-YL)INDOLIN-2-ONE DERIVATIVE

(71) Applicant: Sumitomo Dainippon Pharma Co., Ltd., Osaka (JP)

(72) Inventors: Akihito Nonoyama, Osaka (JP); Kazuki Hashimoto, Osaka (JP)

(73) Assignee: SUMITOMO DAINIPPON PHARMA CO., LTD., Osaka (JP)

( * ) Notice: Subject to any disclaimer, the term of this patent is extended or adjusted under 35 U.S.C. 154(b) by 0 days.

(21) Appl. No.: 15/751,014

(22) PCT Filed: Aug. 9, 2016

(86) PCT No.: PCT/JP2016/003667
§ 371 (c)(1),
(2) Date: Feb. 7, 2018

(87) PCT Pub. No.: WO2017/026119
PCT Pub. Date: Feb. 16, 2017

(65) Prior Publication Data
US 2018/0230141 A1    Aug. 16, 2018

(30) Foreign Application Priority Data
Aug. 10, 2015  (JP) ................. 2015-158135

(51) Int. Cl.
*C07D 417/14* (2006.01)
*A61K 31/427* (2006.01)
*A61K 31/4439* (2006.01)

(52) U.S. Cl.
CPC .......... *C07D 417/14* (2013.01); *A61K 31/427* (2013.01); *A61K 31/4439* (2013.01)

(58) Field of Classification Search
None
See application file for complete search history.

(56) References Cited

FOREIGN PATENT DOCUMENTS

| JP | 63-68543 | 3/1988 |
|---|---|---|
| JP | 2002-167364 | 6/2002 |
| JP | 2010-538091 | 12/2010 |
| WO | 2009/033033 | 3/2009 |
| WO | 2013/140232 | 9/2013 |
| WO | 2013/162390 | 10/2013 |
| WO | 2014/160401 | 10/2014 |

OTHER PUBLICATIONS

International Search Report dated Sep. 27, 2016 in International (PCT) Application No. PCT/JP2016/003667.
Sidoryk et al., "Physicochemical Characteristics of Sunitinib Malate and its Process-Related Impurities", Journal of Pharmaceutical Sciences, vol. 102, No. 2, Feb. 2013, pp. 706-716.
Shin Jikken Kagaku Koza 13 Yuki Kozo [I], vol. 20, Jan. 1977, p. 99.

*Primary Examiner* — Heidi Reese
(74) *Attorney, Agent, or Firm* — Wenderoth, Lind & Ponack, L.L.P.

(57) ABSTRACT

The present invention addresses the problem of providing a purification method for a 5-(thiazol-4-yl)indolin-2-one derivative that is useful as a medication. The present invention provides a purification method for a compound represented by formula (1) (in the formula, each n is independently 2, 3, 4, 5, or 6, $R^1$ and $R^2$ are identical or different and each independently represent a $C_{1-6}$ alkyl group, $R^3$, $R^4$, $R^5$, $R^6$, $R^7$, $R^8$, $R^9$, $R^{10}$, $R^{11}$, $R^{12}$, and $R^{13}$ each represent a hydrogen atom, a $C_{1-6}$ alkyl group, an aryl group, or a heteroaryl group), or a geometric isomer thereof, or a mixture thereof, or a pharmaceutically acceptable salt thereof. The purification method includes a purification step performed using a solid-phase support adsorbent in the presence of a purification solvent.

20 Claims, 1 Drawing Sheet

PURIFICATION METHOD FOR 5-(THIAZOL-4-YL)INDOLIN-2-ONE DERIVATIVE

TECHNICAL FIELD

The present invention is related to a purification method of a 5-(thiazol-4-yl)indolin-2-one derivative or a pharmaceutically acceptable salt thereof useful as a pharmaceutical product.

BACKGROUND ART

Patent Literature 1, listed below, describes that a 5-(thiazol-4-yl)indolin-2-one derivative represented by the following formula (V):

[Chem. 1]

(V)

wherein $R^{1a}$, $R^{2a}$, $R^{3a}$, $R^{4a}$, $R^{5a}$, $R^{6a}$, $R^{7a}$, $R^{8a}$, $R^{9a}$, $R^{10a}$, $R^{11a}$, $R^{12a}$, and $R^{13a}$ are a hydrogen atom, an alkyl group or a substituted alkyl group, an aryl group or a substituted aryl group, or the like, $n_a$ is an integer selected from 2, 3, 4, 5, and 6, are useful for a pharmaceutical product.

Patent Literature 2, listed below, describes a production method of Sunitinib, an indolin-2-one derivative, with the purity thereof improved by reacting ethyl iodide with the compound that is de-ethylated at the terminal amino group of Sunitinib in the presence of a base to ethylate the terminal amino group.

Patent Literature 3, listed below, describes that impurities comprised in a crudely purified product of Sunitinib are reduced by adsorbing the de-ethylated compound of an intermediate for Sunitinib onto silica gel and separating by filtration.

CITATION LIST

Patent Literature

[PTL 1] Japanese Patent No. 5452490
[PTL 2] International Publication No. WO 2013/140232
[PTL 3] International Publication No. WO 2013/162390

SUMMARY OF INVENTION

Solution to Problem

The inventors intensively studied to establish a novel purification method of a 5-(thiazol-4-yl)indolin-2-one derivative represented by formula (1) or a pharmaceutically acceptable salt thereof, which is useful as a pharmaceutical product, and consequently accomplished the completion of the present invention. Accordingly, the present invention provides a purification method of a 5-(thiazol-4-yl)indolin-2-one derivative represented by formula (1) or a pharmaceutically acceptable salt thereof, which is useful as a pharmaceutical product.

Specifically, the present invention is as described below.

[Item 1]

A purification method of a compound represented by formula (1):

[Chem. 2]

(1)

wherein:

$R^1$ and $R^2$ may be identical or different and are each independently an alkyl group or a substituted alkyl group;

$R^3$ is a hydrogen atom, an alkyl group, a substituted alkyl group, a cycloalkyl group, a substituted cycloalkyl group, an aryl group, a substituted aryl group, a heteroaryl group, or a substituted heteroaryl group, or $R^1$ or $R^2$ and $R^3$ are taken together with the nitrogen atom to which they are attached to form a heterocycle or a substituted heterocycle;

$R^4$ and $R^7$ may be identical or different and are each independently a hydrogen atom, an alkyl group, a substituted alkyl group, a cycloalkyl group, a substituted cycloalkyl group, a heterocyclic group, a substituted heterocyclic group, an aryl group, a substituted aryl group, a heteroaryl group, or a substituted heteroaryl group;

$R^5$ is a hydrogen atom, an alkyl group, a substituted alkyl group, a cycloalkyl group, a substituted cycloalkyl group, an aryl group, a substituted aryl group, a heteroaryl group, or a substituted heteroaryl group;

$R^6$ and $R^{12}$ may be identical or different and are each independently a hydrogen atom, a halogen atom, a cyano group, a nitro group, a trifluoromethyl group, a trifluoromethyloxy group, an alkyl group, a substituted alkyl group, a cycloalkyl group, a substituted cycloalkyl group, a heterocyclic group, a substituted heterocyclic group, an aryl group, a substituted aryl group, —$OR^a$, a heteroaryl group, or a substituted heteroaryl group;

$R^8$ is a hydrogen atom, an alkyl group, a substituted alkyl group, an alkenyl group, a substituted alkenyl group, an alkynyl group, a substituted alkynyl group, a cycloalkyl group, a substituted cycloalkyl group, a cycloalkenyl group, a substituted cycloalkenyl group, a heterocyclic group, a substituted heterocyclic group, an aryl group, a substituted aryl group, a heteroaryl group, a substituted heteroaryl group, —$OR^a$, —$SR^a$, —$S(=O)_2R^e$, —$S(=O)_2OR^e$, —$C(=O)OR^d$, —$C(=O)R^a$, or —$C(=O)NR^bR^c$;

$R^9$, $R^{10}$, and $R^{11}$ may be identical or different and are each independently a hydrogen atom, a halogen atom, a cyano group, a nitro group, a trifluoromethyl group, a trifluoromethyloxy group, an alkyl group, a substituted alkyl group, an alkenyl group, a substituted alkenyl group, an alkynyl group, a substituted alkynyl group, a cycloalkyl group, a substituted cycloalkyl group, a cycloalkenyl group, a substituted cycloalkenyl group, a heterocyclic group, a substituted heterocyclic group, an aryl group, a substituted aryl group, a heteroaryl group, a substituted heteroaryl group, —OR$^a$, —SR$^a$, —S(=O)R$^e$, —S(=O)$_2$R$^e$, —P(=O)$_2$R$^e$, —S(=O)$_2$OR$^e$, —P(=O)$_2$OR$^e$, —NR$^b$R$^e$, —NR$^b$S(=O)$_2$R$^e$, —NR$^b$P(=O)$_2$R$^e$, —S(=O)$_2$NR$^b$R$^c$, —P(=O)$_2$NR$^b$R$^c$, —C(=O)OR$^e$, —C(=O)R$^a$, —C(=O)NR$^b$R$^c$, —OC(=O)R$^a$, —OC(=O)NR$^b$R$^c$, —NR$^b$C(=O)OR$^e$, —NR$^d$C(=O)NR$^b$R$^c$, —NR$^d$S(=O)$_2$NR$^b$R$^c$, —NR$^d$P(=O)$_2$NR$^b$R$^c$, or —NR$^{13}$C(=O)R$^a$;

R$^{13}$ is a hydrogen atom, an alkyl group, a substituted alkyl group, a cycloalkyl group, a substituted cycloalkyl group, a heterocyclic group, a substituted heterocyclic group, an aryl group, a substituted aryl group, a heteroaryl group, or a substituted heteroaryl group;

n is an integer selected from 2, 3, 4, 5, and 6;

each R$^a$ is independently a hydrogen atom, an alkyl group, a substituted alkyl group, an alkenyl group, a substituted alkenyl group, an alkynyl group, a substituted alkynyl group, a cycloalkyl group, a substituted cycloalkyl group, a cycloalkenyl group, a substituted cycloalkenyl group, a heterocyclic group, a substituted heterocyclic group, an aryl group, or a substituted aryl group;

R$^b$, R$^c$, and R$^d$ may be identical or different and are each independently a hydrogen atom, an alkyl group, a substituted alkyl group, a cycloalkyl group, a substituted cycloalkyl group, a heterocyclic group, a substituted heterocyclic group, an aryl group, or a substituted aryl group, or said R$^b$ and R$^c$ are optionally taken together with the nitrogen atom to which they are attached to form a heterocycle or a substituted heterocycle;

each R$^e$ is independently an alkyl group, a substituted alkyl group, an alkenyl group, a substituted alkenyl group, an alkynyl group, a substituted alkynyl group, a cycloalkyl group, a substituted cycloalkyl group, a cycloalkenyl group, a substituted cycloalkenyl group, a heterocyclic group, a substituted heterocyclic group, an aryl group, or a substituted aryl group; and the wavy line represents either cis or trans, or a geometrical isomer thereof, or a mixture thereof, or a pharmaceutically acceptable salt thereof, wherein the method comprises a step of removing a compound represented by the following formula (7):

[Chem. 3]

(7)

wherein n, R$^3$, R$^4$, R$^5$, R$^6$, R$^7$, R$^8$, R$^9$, R$^{10}$, R$^{11}$, R$^{12}$, R$^{13}$, and the wavy line are defined the same as in the compound represented by formula (1), and R$^{14}$ is an alkyl group or a substituted alkyl group, or R$^{14}$ and R$^3$ are taken together with the nitrogen atom to which they are attached to form a heterocycle or a substituted heterocycle, or a geometrical isomer thereof, or a mixture thereof, or a pharmaceutically acceptable salt thereof by using a solid-phase supported adsorbent in the presence of a purification solvent.

[Item 2]

The purification method according to item 1, wherein:

R$^1$ and R$^2$ may be identical or different and are each independently a C$_{1-6}$alkyl group, R$^3$, R$^4$, R$^5$, R$^6$, R$^7$, R$^8$, R$^9$, R$^{10}$, R$^{11}$, R$^{12}$, and R$^{13}$ may be identical or different and are each independently a hydrogen atom, a C$_{1-6}$alkyl group, a substituted C$_{1-6}$alkyl group, a C$_{3-6}$cycloalkyl group, a substituted C$_{3-6}$cycloalkyl group, a C$_{6-10}$aryl group, a substituted C$_{6-10}$aryl group, a 5- to 10-membered heteroaryl group, or a 5- to 10-membered substituted heteroaryl group, and R$^{14}$ is a C$_{1-6}$alkyl group; or R$^1$ or R$^2$ and R$^3$ are taken together with the nitrogen atom to which they are attached to form a 6- to 10-membered heterocycle or substituted heterocycle, R$^4$, R$^5$, R$^6$, R$^7$, R$^8$, R$^9$, R$^{10}$, R$^{11}$, R$^{12}$, and R$^{13}$ may be identical or different and are each independently a hydrogen atom, a C$_{1-6}$alkyl group, a substituted C$_{1-6}$alkyl group, a C$_{3-6}$cycloalkyl group, a substituted C$_{3-6}$cycloalkyl group, a C$_{6-10}$aryl group, a substituted C$_{6-10}$aryl group, a 5- to 10-membered heteroaryl group, or a 5- to 10-membered substituted heteroaryl group, and R$^{14}$ and R$^3$ are taken together with the nitrogen atom to which they are attached to form a 6- to 10-membered heterocycle or substituted heterocycle.

[Item 3]

The purification method according to item 1 or 2, wherein R$^1$ and R$^2$ may be identical or different and are each independently a C$_{1-6}$alkyl group, R$^3$, R$^4$, R$^5$, R$^6$, R$^7$, R$^8$, R$^9$, R$^{10}$, R$^{11}$, R$^{12}$, and R$^{13}$ may be identical or different and are each independently a hydrogen atom, a C$_{1-6}$alkyl group, a C$_{6-10}$aryl group, or a 5- to 10-membered heteroaryl group, and R$^{14}$ is a C$_{1-6}$alkyl group.

[Item 4]

The purification method according to any one of items 1 to 3, wherein the purification solvent is an oxidation-non-inducing solvent.

[Item 5]

The purification method according to any one of items 1 to 4, wherein the purification is carried out under a nitrogen atmosphere.

[Item 6]

The purification method according to any one of items 1 to 5, wherein the adsorption portion of the solid-phase supported adsorbent is toluenesulfonyl chloride, sulfonic acid, toluenesulfonic acid, isocyanate, or carbodiimide.

[Item 7]

The purification method according to item 6, wherein the adsorption portion of the solid-phase supported adsorbent is toluenesulfonyl chloride.

[Item 8]

The purification method according to any one of items 1 to 7, wherein the solid-phase portion of the solid-phase supported adsorbent is polystyrene.

[Item 9]

The purification method according to any one of items 1 to 8, wherein R$^1$ and R$^2$ may be identical or different and are each independently a C$_{1-3}$alkyl group.

[Item 10]

The purification method according to item 9, wherein R$^1$ and R$^2$ are both ethyl groups.

[Item 11]
The purification method according to any one of items 1 to 10, wherein $R^{13}$ is an aryl group.

[Item 12]
The purification method according to item 11, wherein $R^{13}$ is a phenyl group.

[Item 13]
The purification method according to any one of items 1 to 12, wherein $R^4$ and $R^6$ may be identical or different and are each independently a $C_{1-6}$alkyl group.

[Item 14]
The purification method according to item 13, wherein $R^4$ and $R^6$ may be identical or different and are each independently a $C_{1-3}$alkyl group.

[Item 15]
The purification method according to any one of items 1 to 14, wherein $R^3$ and $R^5$ are both hydrogen atoms.

[Item 16]
The purification method according to any one of items 1 to 15, wherein $R^7$, $R^8$, $R^9$, $R^{10}$, $R^{11}$, and $R^{12}$ are all hydrogen atoms.

[Item 17]
The purification method according to any one of items 1 to 16, wherein the method comprises a step of reacting a crudely purified product comprising the compound represented by formula (1) with the solid-phase supported adsorbent, then separating the solid-phase supported adsorbent by filtration, and further adding a crystallization solvent to crystallize the compound represented by formula (1).

[Item 18]
The purification method according to any one of items 1 to 17, wherein the proportion of the compound represented by formula (7) in a crudely purified product of the compound represented by formula (1) is 0.1% by weight or less.

[Item 19]
The purification method according to item 18, wherein the proportion of the compound represented by formula (7) in the crudely purified product of the compound represented by formula (1) is 0.05% by weight or less.

[Item 20]
The purification method according to any one of items 1 to 19, wherein the removal ratio of the compound represented by formula (7) is 80% or greater.

[Item 21]
A mixture of a compound represented by formula (1) and a compound represented by formula (7), wherein the compound represented by formula (7) is less than 0.13% in relation to the compound represented by formula (1).

[Item 22]
A pharmaceutical composition comprising a compound represented by formula (1), wherein a compound represented by formula (7) is comprised at less than 0.13% in relation to the compound represented by formula (1).

[Item 23]
A pharmaceutical composition comprising a compound represented by formula (1), wherein the compound represented by formula (1) is comprised at 99.95% or greater over the compound represented by formula (1) and a compound represented by formula (7).

[Item 24]
A pharmaceutical composition comprising a compound represented by formula (1), wherein the compound represented by formula (1) is comprised at 99.98% or greater over the compound represented by formula (1) and a compound represented by formula (7).

[Item 25]
A pharmaceutical composition comprising a compound represented by formula (1), wherein the compound represented by formula (1) is comprised at 99.8% or greater over the pharmaceutical composition comprising the compound represented by formula (1).

[Item 26]
A pharmaceutical composition comprising a compound represented by formula (1), wherein the compound represented by formula (1) is comprised at 99.9% or greater over the pharmaceutical composition comprising the compound represented by formula (1).

[Item 27]
A pharmaceutical composition comprising a compound represented by formula (1), wherein the compound represented by formula (1) is comprised at 99.8% or greater over the total of the compound represented by formula (1) and an analogous substance thereof.

[Item 28]
A pharmaceutical composition comprising a compound represented by formula (1), wherein the compound represented by formula (1) is comprised at 99.9% or greater over the total of the compound represented by formula (1) and an analogous substance thereof.

In the present invention, it is intended that in addition to the clarified combinations, the above-mentioned one or more characteristics can be further combined, and the combination can be further provided. These further embodiments and advantages of the present invention will be recognized by those skilled in the art if the following detailed descriptions are read and understood as necessary.

Advantageous Effects of Invention

By the present invention, a novel purification method of a compound represented by formula (1) useful as a pharmaceutical product can be provided. The present invention also enables easy removal of a compound represented by formula (7) from a crudely purified product of a compound represented by formula (1), which compound represented by formula (7) is so similar in structure and physical properties that its removal has been difficult. The purification method is a useful method in which the operation in purification is simple and easy, the amount of byproducts produced is small, and a compound represented by formula (1) can be provided in a high yield.

DESCRIPTION OF EMBODIMENTS

Hereinafter, the present invention will be explained while showing its preferred embodiments. Throughout the entire specification, a singular expression should be understood as encompassing the concept thereof in the plural form, unless specifically noted otherwise. Thus, singular articles (e.g., "a", "an", "the" and the like in case of English) should also be understood as encompassing the concept thereof in the plural form unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the terms commonly understood by those skilled in the art to which the present invention pertains. In case of a contradiction, the present specification (including the definitions) takes precedence.

The definitions of each term and each substituent in the present specification are as follows.

The carbon number in the definition of a "substituent" in the present specification may be expressed as, for example, "$C_{1-6}$" or the like. Specifically, the expression "$C_{1-6}$alkyl group" is synonymous with an alkyl group having a carbon number from 1 to 6. In addition, in the present specification, a substituent for which the terms "substitution", "optionally substituted", or "substituted" are not particularly and explicitly described, means the "unsubstituted" substituent. For example, a "$C_{1-6}$alkyl group" means to be "unsubstituted".

In the present specification, the term "group" refers to a monovalent group. For example, an "alkyl group" refers to a monovalent saturated hydrocarbon group. In addition, in the description of a substituent in the present specification, the term "group" may be omitted. It should be noted that the number of substituents of a group defined by "substitution", "optionally substituted", or "substituted" is not particularly limited as long as it is substitutable, and is one or plural. Moreover, unless otherwise indicated, the description for each group is also applied when the group is one part of or a substituent on another group.

An "alkyl group" refers to any linear or branched alkyl group. Although the carbon number of an alkyl group is not limited, examples thereof can include $C_{1-12}$, $C_{1-10}$, $C_{1-6}$, $C_{1-6}$, $C_{1-4}$ $C_{1-3}$, and the like. A "$C_{1-6}$alkyl group" refers to a linear or branched alkyl group having a carbon number from 1 to 6, and specific examples thereof include a methyl group, an ethyl group, a n-propyl group, an isopropyl group, a n-butyl group, an isobutyl group, a sec-butyl group, a tert-butyl group, a pentyl group, an isopentyl group, a neopentyl group, and a n-hexyl group, as well as structural isomers thereof. Among these, a $C_{1-4}$alkyl group is preferable, and a $C_{1-3}$alkyl group is more preferable. Specific examples thereof include a methyl group, an ethyl group, a n-propyl group, and an isopropyl group. Among these, a methyl group and an ethyl group are preferable.

A "substituted alkyl group" refers to an alkyl group substituted with a substituent as described below. Preferably, it is a "substituted $C_{3-6}$ alkyl group". Examples of the substituted alkyl group include an aminoethyl group, a methoxypropyl group, an acetoxybutyl group, and a chloropentyl group. A "substituted $C_{3-6}$ alkyl group" refers to a $C_{3-6}$ alkyl group substituted with a substituent as described below. Examples of the substituted $C_{3-6}$alkyl group include an aminopropyl group, a methoxypropyl group, an acetoxypropyl group, and a chloropropyl group.

A "cycloalkyl group" refers to a saturated cyclic hydrocarbon group. Preferably, it has a carbon number from 3 to 7, and more preferably is a "$C_{3-6}$cycloalkyl group". Specific examples of the "cycloalkyl group" include, for example, cyclopropyl, cyclobutyl, cyclopentyl, cyclohexyl, and the like.

A "substituted cycloalkyl group" refers to a cycloalkyl group substituted with a substituent as described below. Preferably, it is a "substituted $C_{3-6}$cycloalkyl group". Examples of the substituted cycloalkyl group include an aminocyclobutyl group, a methoxycyclopentyl group, an acetoxycyclopentyl group, and a chlorocyclohexyl group.

A "substituted $C_{3-6}$cycloalkyl group" refers to a $C_{3-6}$cycloalkyl group substituted with a substituent as described below. Examples of the substituted $C_{3-6}$cycloalkyl group include an aminocyclobutyl group, a methoxycyclopropyl group, an acetoxycyclopentyl group, and a chlorocyclohexyl group.

An "alkenyl group" refers to a linear or branched, unsaturated aliphatic hydrocarbon group having one or more double bonds, and examples thereof include an ethenyl group, a propenyl group, a crotyl group, a butenyl group, a pentenyl group, and a hexenyl group, as well as structural isomers and geometrical isomers thereof. Preferably, it is an alkenyl group having a carbon number from 2 to 6. A double bond in the "alkenyl group" may be at any position on the carbon chain. Preferably, it is a $C_{2-6}$alkenyl group, and more preferably a $C_{2-3}$alkenyl group.

A "substituted alkenyl group" refers to an alkenyl group substituted with a substituent as described below. Examples of the substituted alkenyl group include an aminoethenyl group, a methoxypropenyl group, an acetoxycrotyl group, and a chloropentenyl group.

A "cycloalkenyl group" refers to an unsaturated cyclic hydrocarbon group. Preferably, it has a carbon number from 3 to 7, and more preferably is a "$C_{3-6}$ cycloalkenyl group". Specific examples of the "cycloalkenyl group" include, for example, cyclobutenyl, cyclopentenyl, cyclohexenyl, and the like.

A "substituted cycloalkenyl group" refers to a cycloalkenyl group substituted with a substituent as described below. Examples of the substituted cycloalkenyl group include an aminocyclobutenyl group, a methoxycyclopentenyl group, an acetoxycyclopentenyl group, and a chlorocyclohexenyl group.

An "alkynyl group" refers to a linear or branched, unsaturated aliphatic hydrocarbon group having one or more triple bonds, and examples thereof include an ethynyl group, a propynyl group, a butynyl group, a pentynyl group, and a hexynyl group, as well as structural isomers thereof. Preferably, it is an alkynyl group having a carbon number from 2 to 6. A triple bond in the "alkynyl group" may be at any position on the carbon chain. Preferably, it is a $C_{2-6}$alkynyl group, and more preferably a $C_{2-3}$alkynyl group.

A "substituted alkynyl group" refers to an alkynyl group substituted with a substituent as described below. Examples of the substituted alkynyl group include an aminoethynyl group, a methoxypropynyl group, an acetoxybutynyl group, and a chloropentynyl group.

An "aryl group" is a monocyclic or multicyclic 6- to 14-membered aromatic hydrocarbon group, preferably a 6- or 10-membered aromatic hydrocarbon group, more preferably a 6-membered aromatic hydrocarbon group. Specific examples thereof include a phenyl group, a naphthyl group, a phenanthryl group, an anthryl group, a fluorenyl group, a tetrahydronaphthyl group, an indenyl group, and an indanyl group. Among these, a phenyl group and a naphthyl group are preferable and a phenyl group is particularly preferable.

A "substituted aryl group" refers to an aryl group substituted with a substituent as described below. Preferably, it is a "substituted $C_{6-10}$aryl group". Examples of the substituted aryl group include an aminophenyl group, a methoxyphenyl group, an acetoxynaphthyl group, and a chloroanthracenyl group.

A "substituted $C_{6-10}$aryl group" refers to a $C_{6-10}$aryl group substituted with a substituent as described below. Examples of the substituted $C_{6-10}$aryl group include an aminophenyl group, a methoxyphenyl group, an acetoxynaphthyl group, and a chloronaphthyl group.

A "heteroaryl group" refers to a monocyclic or multicyclic 5- to 10-membered aromatic hydrocarbon group containing a heteroatom such as nitrogen, oxygen, sulfur, and the like, and preferably a 5- or 6-membered aromatic hydrocarbon group containing a heteroatom such as nitrogen, oxygen, sulfur, and the like. Specific examples thereof include a furyl group, a benzofuranyl group, a thienyl group, a benzothiophenyl group, a pyrrolyl group, a pyridyl group, an indolyl group, an oxazolyl group, a benzoxazolyl group, an isoxazolyl group, a benzisoxazolyl group, a thiazolyl group, a benzothiazolyl group, an isothiazolyl group, an imidazolyl group, a benzimidazolyl group, a pyrazolyl group, an indazolyl group, a tetrazolyl group, a furazanyl group, a 1,2,3-oxadiazolyl group, a 1,2,3-thiadiazolyl group, a 1,2,4-thiadiazolyl group, a 1,2,3-triazolyl group, a 1,2,4-triazolyl group, a benzotriazolyl group, a quinolinyl group, an isoquinolinyl group, a pyridazinyl group, a pyrimidinyl group, a purinyl group, a pyrazinyl group, a pteridinyl group, a phenoxazolyl group, a benzopyrazolyl group, a quinolizinyl group, a cinnolinyl group, a phthalazinyl group, a quinazolinyl group, and a quinoxalinyl group. Among these, a furyl group, a pyrrolyl group, a pyridyl group, an indolyl group, a thiazolyl group, an imidazolyl group, and a pyrimidinyl group are preferable.

A "substituted heteroaryl group" refers to a heteroaryl group substituted with a substituent as described below. Preferably, it is a "5- to 10-membered substituted heteroaryl group". Examples of the substituted heteroaryl group include an aminopyridinyl group, a methoxyfuranyl group, an acetoxythiophenyl group, and a chloroindolyl group.

A "5- to 10-membered substituted heteroaryl group" refers to a 5- to 10-membered heteroaryl group substituted with a substituent as described below. Examples of the 5- to 10-membered substituted heteroaryl group include an aminopyridinyl group, a methoxyfuranyl group, an acetoxythiophenyl group, and a chloroindolyl group.

Examples of a "halogen atom" include a fluorine atom, a chlorine atom, a bromine atom, an iodine atom, and the like. Preferably, it is a fluorine atom or a chlorine atom.

Examples of a "heterocyclic group" include a cyclic group of a 3- to 7-membered, saturated or unsaturated aliphatic ring having one to three homogeneous or heterogeneous atoms selected from a nitrogen atom, an oxygen atom, and a sulfur atom, and the like. All of the above-described nitrogen atom, oxygen atom, and sulfur atom are atoms constituting a ring. The heterocyclic group may be either saturated or unsaturated. Specific examples thereof include a pyranyl group, a tetrahydrofuryl group, a pyrrolidinyl group, an imidazolidinyl group, a piperidinyl group, a morpholinyl group, a thiomorpholinyl group, a dioxothiomorpholinyl group, a hexamethyleneiminyl group, an oxazolidinyl group, a thiazolidinyl group, an imidazolidinyl group, an oxoimidazolidinyl group, an dioxoimidazolidinyl group, an oxooxazolidinyl group, an dioxooxazolidinyl group, a dioxothiazolidinyl group, a tetrahydrofuranyl group, a tetrahydropyridinyl group, and the like.

The above-described "heterocyclic group" may form a fused ring with a 6-membered aromatic hydrocarbon ring or a 6-membered unsaturated heterocycle containing a heteroatom such as nitrogen, oxygen, sulfur, and the like. Examples thereof include a bicyclic 9- or 10-membered "heterocyclic group" in which the above-mentioned 5- or 6-membered "heterocyclic group" is fused to a 6-membered aromatic hydrocarbon ring or a 6-membered unsaturated heterocycle. Examples of the 6-membered aromatic hydrocarbon ring include benzene and the like. Examples of the 6-membered unsaturated heterocycle include a pyridine ring, a pyrimidine ring, a pyridazine ring, and the like. Specific examples of the "heterocyclic group" forming the above-described fused ring include a dihydroindolyl group, a dihydroisoindolyl group, a dihydropurinyl group, a dihydrothiazolopyrimidinyl group, a dihydrobenzodioxanyl group, an isoindolinyl group, an indazolyl group, tetrahydroquinolinyl group, a decahydroquinolinyl group, a tetrahydroisoquinolinyl group, a decahydroisoquinolinyl group, a tetrahydronaphthyridinyl group, a tetrahydropyridoazepinyl group, and the like. For the "heterocyclic group", a saturated heterocyclic group is preferable, and a 5- or 6-membered saturated heterocyclic group is preferable.

A "heterocycle" refers to a ring corresponding to the above-described "heterocyclic group", and a 3- to 7-membered, saturated or unsaturated aliphatic ring having one to three homogeneous or heterogeneous atoms selected from the group consisting of an oxygen atom, a sulfur atom, and a nitrogen atom as a ring-constituting atom. Examples of thereof include a pyrrolidine ring, a piperidine ring, and a piperazine ring.

In the present specification, for further "substitution" or "substituted" in each substituent, any suitable substituent can be used. Examples of a substituent, for example, in the "substituted alkyl group", the "substituted alkenyl group", the "substituted alkynyl group", the "substituted aryl group", the "substituted heteroaryl group", the "substituted cycloalkyl group", the "substituted cycloalkenyl group", and the "substituted heterocyclic group" include one or more substituents selected from the group consisting of a halogen atom, a hydroxyl group, an amino group, a cyano group, a nitro group, a $C_{1-6}$alkylcarbamoyl group, an acyl group, a $C_{1-6}$alkyloxy group, a $C_{1-6}$alkyl group, a mono- or di-$C_{1-6}$alkylamino group, a $C_{1-6}$alkylsulfanyl group, a $C_{1-6}$alkylsulfinyl group, a $C_{1-6}$alkylsulfonyl group, a sulfamoyl group, and a trifluoromethyl group. Substitution with each of the above-mentioned substituents can occur at any substitutable position on a substituent to be substituted.

A "carboxyl-based leaving group" refers to a substituted carbonyloxy group (a substituent of the carbonyloxy group is not particularly limited as long as it is chemically stable). Specific examples thereof include an acetyloxy group, a trifluoroacetyloxy group, a trichloroacetyloxy group, and the like.

A "sulfonyl-based leaving group" refers to a substituted sulfonyloxy group (a substituent of the sulfonyloxy group is not particularly limited as long as it is chemically stable). Specific examples thereof include a methanesulfonyloxy group, a trifluoromethanesulfonyloxy group, a benzenesulfonyloxy group, a toluenesulfonyloxy group, and the like.

A "purification solvent" refers to a solvent used in purification of a compound represented by formula (1) from a crudely purified product comprising the compound represented by formula (1). Representative examples of the purification solvent include, but not limited to, oxidation-non-inducing solvents. An "oxidation-non-inducing solvent" is a solvent that is unlikely to cause oxidation, and specific examples thereof include N,N-dimethylacetamide, N,N-dimethylformamide, formamide, N-methylpyrrolidinone, and the like. It is preferable that a purification solvent is sufficiently degassed to make the concentration of oxygen molecule low.

A "crystallization solvent" refers to a solvent used in crystallization after purification by a solid-phase supported adsorbent. Examples of the crystallization solvent include, preferably, methanol, ethanol, 2-propanol, acetonitrile, methyl acetate, ethyl acetate, isopropyl acetate, toluene, acetone, and methyl ethyl ketone.

An "analogous substance" refers to a substance that has the same carbon skeleton (a portion where carbons are bound to each other) as a certain substance but has a different substituent from the certain substance. Accordingly, a compound represented by formula (7) is one of analogous substances of a compound represented by formula (1) of the present invention. A purity of a compound represented by formula (1) "over the total of the compound represented by formula (1) and an analogous substance thereof" as used herein refers to a percentage of the compound represented by formula (1) with respect to the total of the compound represented by formula (1) and a group of analogous substances represented by formula (7). In one embodiment, said purity is 99.80% or greater, 99.85% or greater, 99.90% or greater, or 99.95% or greater.

In addition, in another embodiment, a purity of a compound represented by formula (1) "over the compound represented by formula (1) and a compound represented by formula (7)" refers to a percentage of the compound represented by formula (1) with respect to the total of the compound represented by formula (1) and the compound represented by formula (7). In one embodiment, said purity is 99.94% or greater, 99.95% or greater, 99.96% or greater, 99.97% or greater, 99.98% or greater, or 99.99% or greater.

In yet another embodiment, a purity of a compound represented by formula (7) "in relation to the compound represented by formula (1)" refers to a percentage of the compound represented by formula (7) with respect to the compound represented by formula (1). In one embodiment, said purity is less than 0.07%, less than 0.06%, less than 0.05%, less than 0.04%, less than 0.03%, less than 0.02%, or less than 0.01%.

In the present specification, n is 2, 3, 4, 5, or 6, preferably 2, 3, 4, or 5, and further preferably 2.

In the present specification, $R^1$ and $R^2$ may be identical or different and are each independently an alkyl group, or a substituted alkyl group, and preferably may be identical or different and are each independently a $C_{1-6}$alkyl group, preferably a $C_{1-3}$alkyl group, and further preferably an ethyl group.

$R^3$ is a hydrogen atom, an alkyl group, a substituted alkyl group, a cycloalkyl group, a substituted cycloalkyl group, an aryl group, a substituted aryl group, a heteroaryl group, or a substituted heteroaryl group, or $R^1$ or $R^2$ and $R^3$ are taken together with the nitrogen atom to which they are attached to form a heterocycle or a substituted heterocycle, preferably, $R^3$ is a hydrogen atom or a $C_{1-6}$alkyl group, and more preferably a hydrogen atom.

$R^4$ and $R^7$ may be identical or different and are each independently a hydrogen atom, an alkyl group, a substituted alkyl group, a cycloalkyl group, a substituted cycloalkyl group, a heterocyclic group, a substituted heterocyclic group, an aryl group, a substituted aryl group, a heteroaryl group, or a substituted heteroaryl group, and preferably may be identical or different and are each independently a hydrogen atom or a $C_{1-6}$alkyl group. More preferably, $R^4$ is a $C_{1-6}$alkyl group and $R^7$ is a hydrogen atom.

$R^5$ is a hydrogen atom, an alkyl group, a substituted alkyl group, a cycloalkyl group, a substituted cycloalkyl group, an aryl group, a substituted aryl group, a heteroaryl group, or a substituted heteroaryl group, preferably a hydrogen atom or a $C_{1-6}$alkyl group, and more preferably a hydrogen atom.

$R^6$ and $R^{12}$ may be identical or different and are each independently a hydrogen atom, a halogen atom, a cyano group, a nitro group, a trifluoromethyl group, a trifluoromethyloxy group, an alkyl group, a substituted alkyl group, a cycloalkyl group, a substituted cycloalkyl group, a heterocyclic group, a substituted heterocyclic group, an aryl group, a substituted aryl group, $-OR^a$, a heteroaryl group, or a substituted heteroaryl group, and preferably may be identical or different and are each independently a hydrogen atom or a $C_{1-6}$alkyl group. More preferably, $R^6$ is a $C_{1-6}$alkyl group, and $R^{12}$ is a hydrogen atom.

$R^8$ is a hydrogen atom, an alkyl group, a substituted alkyl group, an alkenyl group, a substituted alkenyl group, an alkynyl group, a substituted alkynyl group, a cycloalkyl group, a substituted cycloalkyl group, a cycloalkenyl group, a substituted cycloalkenyl group, a heterocyclic group, a substituted heterocyclic group, an aryl group, a substituted aryl group, a heteroaryl group, a substituted heteroaryl group, $-OR^a$, $-SR^a$, $-S(=O)_2R^e$, $-S(=O)_2OR^e$, $-C(=O)OR^d$, $-C(=O)R^a$, or $-C(=O)NR^bR^c$, preferably a hydrogen atom or a $C_{1-6}$alkyl group, and more preferably a hydrogen atom.

$R^9$, $R^{10}$, and $R^{11}$ may be identical or different and are each independently a hydrogen atom, a halogen atom, a cyano group, a nitro group, a trifluoromethyl group, a trifluoromethyloxy group, an alkyl group, a substituted alkyl group, an alkenyl group, a substituted alkenyl group, an alkynyl group, a substituted alkynyl group, a cycloalkyl group, a substituted cycloalkyl group, a cycloalkenyl group, a substituted cycloalkenyl group, a heterocyclic group, a substituted heterocyclic group, an aryl group, a substituted aryl group, a heteroaryl group, a substituted heteroaryl group, $-OR^a$, $-SR^a$, $-S(=O)R^e$, $-S(=O)_2R^e$, $-P(=O)_2R^e$, $-S(=O)_2OR^e$, $-P(=O)_2OR^e$, $-NR^bR^c$, $-NR^bS(=O)_2R^e$, $-NR^bP(=O)_2R^e$, $-S(=O)_2NR^bR^c$, $-P(=O)_2NR^bR^c$, $-C(=O)OR^e$, $-C(=O)R^a$, $-C(=O)NR^bR^c$, $-OC(=O)R^a$, $-OC(=O)NR^bR^c$, $-NR^bC(=O)OR^e$, $-NR^dC(=O)NR^bR^c$, $-NR^dS(=O)_2NR^bR^c$, $-NR^dP(=O)_2NR^bR^c$, or $-NR^bC(=O)R^a$, preferably may be identical or different and are each independently a hydrogen atom or a $C_{1-6}$alkyl group, and more preferably may be identical or different and are each independently a hydrogen atom.

$R^{13}$ is a hydrogen atom, an alkyl group, a substituted alkyl group, a cycloalkyl group, a substituted cycloalkyl group, a heterocyclic group, a substituted heterocyclic group, an aryl group, a substituted aryl group, a heteroaryl group, or a substituted heteroaryl group, preferably an aryl group, and more preferably a phenyl group.

Each $R^a$ is independently a hydrogen atom, an alkyl group, a substituted alkyl group, an alkenyl group, a substituted alkenyl group, an alkynyl group, a substituted alkynyl group, a cycloalkyl group, a substituted cycloalkyl group, a cycloalkenyl group, a substituted cycloalkenyl group, a heterocyclic group, a substituted heterocyclic group, an aryl group, or a substituted aryl group, preferably may be identical or different and is independently a hydrogen atom or a $C_{1-6}$alkyl group, and more preferably may be identical or different and is independently a hydrogen atom.

$R^b$, $R^c$, and $R^d$ may be identical or different and are each independently a hydrogen atom, an alkyl group, a substituted alkyl group, a cycloalkyl group, a substituted cycloalkyl group, a heterocyclic group, a substituted heterocyclic group, an aryl group, or a substituted aryl group, or $R^b$ and $R^c$ are optionally taken together with the nitrogen atom to which they are attached to form a heterocycle or a substituted heterocycle, preferably may be identical or different and are each independently a hydrogen atom or a $C_{1-6}$alkyl group, and more preferably may be identical or different and are each independently a hydrogen atom.

Each $R^e$ is independently an alkyl group, a substituted alkyl group, an alkenyl group, a substituted alkenyl group, an alkynyl group, a substituted alkynyl group, a cycloalkyl group, a substituted cycloalkyl group, a cycloalkenyl group, a substituted cycloalkenyl group, a heterocyclic group, a substituted heterocyclic group, an aryl group, or a substituted aryl group, preferably may be identical or different and is independently a hydrogen atom or a $C_{1-6}$alkyl group, and more preferably may be identical or different and is independently a hydrogen atom.

In a further preferable embodiment, $R^1$ and $R^2$ may be identical or different and are each independently a $C_{1-6}$alkyl group, preferably a $C_{1-3}$alkyl group, and further preferably an ethyl group. In a further preferable embodiment, $R^3$, $R^4$, $R^5$, $R^6$, $R^7$, $R^8$, $R^9$, $R^{10}$, $R^{11}$, $R^{12}$, and $R^{13}$ are each a hydrogen atom, a $C_{1-6}$alkyl group, an aryl group, or a heteroaryl group, and preferably are each a hydrogen atom or a $C_{1-6}$alkyl group. $R^3$, $R^5$, $R^7$, $R^8$, $R^9$, $R^{10}$, $R^{11}$, and $R^{12}$ are further preferably hydrogen atoms, $R^4$ and $R^6$ are each further preferably a $C_{1-3}$alkyl group, and particularly preferably a methyl group. $R^{13}$ is preferably an aryl group or a heteroaryl group, and preferably an aryl group.

Hereinafter, a compound represented by formula (1) and a production method thereof are described. Specific examples of the compound represented by formula (1) include, but not limited to, the following compounds.

(Z)—N-[2-(dimethylamino)ethyl]-2,4-dimethyl-5-{[2-oxo-5-(2-phenylthiazol-4-yl)indolin-3-ylidene]methyl}-1H-pyrrole-3-carboxamide;

(Z)—N-[2-(diethylamino)ethyl]-2,4-dimethyl-5-{[2-oxo-5-(2-phenylthiazol-4-yl)indolin-3-ylidene]methyl}-1H-pyrrole-3-carboxamide;

(Z)-2,4-dimethyl-5-{[2-oxo-5-(2-phenylthiazol-4-yl)indolin-3-ylidene]methyl}-N-[2-(piperidin-1-yl)ethyl]-1H-pyrrole-3-carboxamide;

(Z)—N-[2-(dimethylamino)ethyl]-2,4-dimethyl-5-({2-oxo-5-[2-(pyridin-2-yl)thiazol-4-yl]indolin-3-ylidene}methyl)-1H-pyrrole-3-carboxamide; and (Z)—N-[3-(dimethylamino)propyl]-2,4-dimethyl-5-{[2-oxo-5-(2-phenylthiazol-4-yl)indolin-3-ylidene]methyl}-1H-pyrrole-3-carboxamide.

An example of a pharmaceutically acceptable salt of the compound represented by formula (1) is a pharmaceutically acceptable acidic salt of the compound represented by formula (1). Specific examples thereof include hydrochloride, hydrobromide, sulfate, nitrate, phosphate, methanesulfonate, p-toluenesulfonate, benzenesulfonate, acetate, trifluoroacetate, propionate, butanoate, heptanoate, nicotinate, maleate, fumarate, citrate, succinate, malonate, malate, oxalate, benzoate, and saccharinate, but they are not limited to these salts.

In the present specification, a compound represented by formula (1) and a pharmaceutically acceptable salt thereof as well as a production intermediate for the compound of formula (1) and a salt thereof encompass a hydrate, a solvate, a stereoisomer, a geometrical isomer, and a tautomer thereof.

Specific examples of a salt used as a production intermediate for a compound represented by formula (1) include hydrochloride, hydrobromide, sulfate, nitrate, phosphate, methanesulfonate, p-toluenesulfonate, benzenesulfonate, acetate, trifluoroacetate, propionate, butanoate, heptanoate, nicotinate, maleate, fumarate, citrate, succinate, malonate, malate, oxalate, benzoate, and saccharinate.

A compound represented by formula (1) can be produced, for example, by a method described in Patent Literature 1, and can be also produced using a compound represented by formula (2) described below as a raw material by the following method. The compound represented by formula (2) is produced by a known method, or a commercially available product (Combi-Blocks, Inc., Wuhan Chemwish Technology Co., Ltd., and the like) can be used.

Production of a Compound Represented by Formula (1)

First Step:

The present step is a step of reacting a compound represented by the following formula (2):

[Chem. 4]

(2)

[wherein $X^1$ is a halogen atom, a carboxyl-based leaving group, or a sulfonyl-based leaving group, and $R^8$, $R^9$, $R^{10}$, $R^{11}$, and $R^{12}$ are defined the same as stated in the compound represented by the above-described formula (1)]

with a compound represented by the following formula (3):

[Chem. 5]

(3)

[wherein $R^{13}$ is defined the same as stated in the compound represented by the above-described formula (1)] in the presence of a solvent to produce a compound represented by the following formula (4):

[Chem. 6]

(4)

[wherein $R^8$, $R^9$, $R^{10}$, $R^{11}$, $R^{12}$, and $R^{13}$ are defined the same as stated in the compound represented by formula (1)]. In the present step, examples of a solvent used are preferably N,N-dimethylacetamide, N,N-dimethylformamide, formamide, N-methylpyrrolidinone, ethanol, methanol, and tetrahydrofuran. The reaction temperature in the present step is preferably 60 to 100° C., and further preferably 70 to 90° C.

Second Step:

The present step is a step of producing a compound represented by formula (1) by reacting the compound represented by formula (4), obtained in the first step, with a compound represented by the following formula (5):

[Chem. 7]

(5)

[wherein n, $R^1$, $R^2$, $R^3$, $R^4$, $R^5$, $R^6$, and $R^7$ are defined the same as stated in the compound represented by formula (1)] in the presence of a base. Examples of a base used in the present step include secondary amines such as piperidine, pyrrolidine, morpholine, diethylamine, and the like, and further preferably pyrrolidine. The reaction temperature in the present step is preferably 60 to 100° C., and further preferably 70 to 90° C. Examples of a solvent used in the present step include N,N-dimethylacetamide, N,N-dimethylformamide, formamide, N-methylpyrrolidinone, tetrahydrofuran. Preferably, it is N-methylpyrrolidinone or tetrahydrofuran.

Production of a Compound Represented by Formula (5)

A compound represented by formula (5) is readily obtained by reacting a compound represented by the following formula (x):

[Chem. 8]

(x)

[wherein n, $R^1$, $R^2$, and $R^3$ are defined the same as stated in the compound represented by formula (1)] with a compound represented by the following formula (y):

[Chem. 9]

(y)

[wherein $R^4$, $R^5$, $R^6$, and $R^7$ are defined the same as stated in the compound represented by formula (1)] in the presence of 1-ethyl-3-(3-dimethylaminopropyl)carbodiimide and 1-hydroxybenzotriazole in a suitable solvent.

Hereinafter, an impurity yielded in producing a compound represented by formula (1) is described.

In the present specification, since a compound represented by the following formula (6):

[Chem. 10]

(6)

[wherein n, $R^3$, $R^4$, $R^5$, $R^6$, $R^7$, and $R^{14}$ are defined the same as stated above] is comprised at 0.1% to 1.0% in the compound represented by formula (5), a corresponding amount of the compound represented by formula (7) is also produced in the reaction system of producing the compound represented by formula (1). Further, in the production process of the compound represented by formula (5), when it is carried out in the presence of oxygen or dimethyl sulfoxide is used as a solvent, the compound represented by formula (6) is oxidatively increased. Accordingly, with regard to the present step, it is preferable to carry out a reaction under low-oxygen condition in a solvent that is hardly influenced by oxidation.

The compound represented by the above-described formula (6) is converted to a compound represented by the following formula (7):

[Chem. 11]

(7)

[wherein n, $R^3$, $R^4$, $R^5$, $R^6$, $R^7$, $R^8$, $R^9$, $R^{10}$, $R^{11}$, $R^{12}$, $R^{13}$, and $R^{14}$ are defined the same as stated above] in the above-described second step. In addition, in the same step, it was found that the compound represented by formula (7) is significantly increased by heating in the presence of oxygen in a solvent, particularly, dimethylsulfoxide. It became clear that a compound represented by formula (7) is comprised in a crudely purified product of a compound represented by formula (1), and further it is difficult to purify the compound represented by formula (7) by a method such as recrystallization, liquid separating operation, and the like. For the above reasons, the compound represented by formula (7) is comprised at 0.1% to 1.0% in the compound represented by formula (1).

Hereinafter, a purification method of the present invention is described.

After a compound represented by formula (1) is dissolved in a purification solvent, addition of a solid-phase supported adsorbent causes a compound represented by formula (7) to be selectively adsorbed. The compound represented by formula (7) can be specifically removed by separating the solid-phase supported adsorbent by filtering operation.

Conventionally, the following points were not disclosed at all: that a compound represented by formula (7) described below, which is an impurity, is comprised in a crudely purified product of a compound represented by formula (1); and that since the impurity is similar in structure and physical properties to the compound represented by formula (1), which is the intended product, it is very difficult to remove the impurity from the crudely purified product of the compound represented by formula (1). Moreover, the following purification method of the present invention was also not disclosed at all: a compound represented by formula (7) comprised in a crudely purified product of a compound represented by formula (1) can be easily removed by using a solid-phase supported adsorbent to provide the compound represented by formula (1) in high purity and a high yield.

A solid-phase supported adsorbent used in the purification method of the present invention is an adsorbent of which the adsorption portion is solid-phase supported. Examples of the adsorption portion include toluenesulfonyl chloride, sulfonic acid, toluenesulfonic acid, isocyanate, and carbodiimide, and it is preferably toluenesulfonyl chloride. Examples of the solid phase of the solid-phase supported adsorbent include polystyrene and silica gel, and it is preferably polystyrene. Specific examples of the solid-phase supported adsorbent include polystyrene sulfonyl chloride (PS-TsCl), and PS-TsCl (made by Biotage® (Trademark)), which is a commercially available product, can be used.

In the purification method of the present invention, examples of a purification solvent used with the above-described solid-phase supported adsorbent include N,N-dimethylacetamide, N,N-dimethylformamide, formamide, and N-methylpyrrolidinone, and it is preferably N,N-dimethylacetamide. The reaction temperature in the reaction with a solid-phase supported adsorbent is preferably 30 to 100° C., and further preferably 50 to 80° C.

The purification method of the present invention may further include a step of separating a solid-phase supported adsorbent by filtering operation and then adding a crystallization solvent to the filtrate to cause crystallization. Examples of the crystallization solvent include, preferably, methanol, ethanol, 2-propanol, acetonitrile, methyl acetate, ethyl acetate, isopropyl acetate, toluene, acetone, and methyl ethyl ketone. It is preferable to stir at 50 to 90° C. after adding a crystallization solvent. The compound represented by formula (1) in high purity can be obtained by, after crystallization, cooling to between 0° C. and 20° C. and filtering the crystal.

In the purification step of the present invention, since the compound represented by formula (7) is oxidatively increased, it is preferable to use the above-described solvent under an atmosphere of inert gas such as nitrogen, argon, and the like.

A removal ratio can be used as an indicator showing how much the compound represented by formula (7) comprised as an impurity in a crudely purified product of the compound represented by formula (1) was able to be removed after the purification. The removal ratio refers to the proportion of the compound represented by formula (7) comprised after purification to the compound represented by formula (7) comprised in a crudely purified product obtained in producing the compound represented by formula (1), and can be expressed as below.

Removal ratio (%)=(1−the amount of the compound represented by formula (7) after the purification/the amount of the compound represented by formula (7) before the purification)×100

The present invention provides a compound represented by formula (1) having high purity; or a composition or a mixture including a compound represented by formula (1) in high purity.

In the present invention, the removal ratio is 40% or greater, preferably 60% or greater, further preferably 80% or greater, and particularly preferably 90% or greater.

"Purity" in the present specification refers to the proportion of the target compound (for example, a compound represented by formula (1)) in a sample, which proportion is determined by quantitative analysis, and representatively refers to the amount or ratio of a compound represented by formula (1) or a pharmaceutically acceptable salt thereof when measured by HPLC or the like. In the present specification, commonly, the purity is based on the "organic" purity of a compound, and does not include measurement values of any amount of water, a solvent, a metal, an inorganic salt, or the like. In a representative embodiment, the purity of a compound represented by formula (1) or a pharmaceutically acceptable salt thereof is compared to the purity of a reference standard material by comparing the areas under the peaks. In the case where the cis/trans-isomers are present in a compound represented by formula (1) or a pharmaceutically acceptable salt thereof, commonly, the purity is calculated by summing these. However, in some cases, one isomer (for example, only cis, or only trans) may be calculated. In one specific embodiment, the purity may be represented by a percentage of a compound represented by formula (1) with respect to the total of the compound represented by formula (1) and a group of analogous substances represented by formula (7), as described in other portions of the present specification. In this case, where the cis/trans-isomers are present in a compound represented by formula (7) or a pharmaceutically acceptable salt thereof, commonly, the purity is calculated by summing these. However, in some cases, one isomer (for example, only cis, or only trans) may be calculated.

In one embodiment, a compound represented by formula (1) or a pharmaceutically acceptable salt thereof has purity greater than about 99.5%. For example, the purity of a compound represented by formula (1) or a pharmaceutically acceptable salt thereof is 99.5% or greater, 99.6% or greater, 99.7% or greater, 99.85% or greater, 99.8% or greater, 99.9% or greater, or 99.95% or greater.

EXAMPLES

Hereinafter, the present invention is described in more detail with examples (including production examples) and comparative examples. However, the technical scope of the present invention is not limited to these examples. In addition, compounds, solvents, time, temperature, weight, equivalent, and the like may be changed within the scope that does not depart from the scope of the present invention. It should be noted that compound names shown in the following examples and comparative examples do not always follow the IUPAC nomenclature.

Production Example 1

Production of a Compound Represented by Formula (1) (A Crudely Purified Product)

Production of (Z)—N-[2-(diethylamino)ethyl]-2,4-dimethyl-5-[(2-oxo-5-(2-phenylthiazol-4-yl)indolin-3-ylidene)methyl]-1H-pyrrole-3-carboxamide (A Crudely Purified Product)

Dimethylformamide (75.0 g) was added to 5-(2-chloroacetyl)indolin-2-one (10.0 g, 47.7 mmol) and thiobenzamide (7.2 g, 52.5 mmol), and then the reaction mixture was heat-stirred at 80° C. After 4 hours, the reaction mixture was cooled to 60° C., and then N-(2-(diethylamino)ethyl)-5-formyl-2,4-dimethyl-1H-pyrrole-3-carboxamide (11.4 g, 42.9 mmol) dissolved in dimethylformamide (57.0 g) was added to the reaction mixture, followed by the addition of pyrrolidine (8.1 g, 114.5 mmol). After 2 hours, acetonitrile (223.0 g) was added dropwise over 30 minutes. After stirring for 30 minutes at the same temperature, the reaction mixture was cooled to 20° C. over 3 hours. The precipitated crystal was filtered, and then the crude crystal was washed with acetonitrile (2×77.4 g) and dried under reduced pressure at 45° C. to yield a crudely purified product of the titled compound (22.6 g, 41.9 mmol). The content of the de-ethylated compound was 0.24%.

Example 1

Purification of the Compound Represented by Formula (1)

Purification of (Z)—N-[2-(diethylamino)ethyl]-2,4-dimethyl-5-[(2-oxo-5-(2-phenylthiazol-4-yl)indolin-3-ylidene)methyl]-1H-pyrrole-3-carboxamide Dimethylacetamide (28.3 g) was added to the crystal (3.00 g, 5.6 mmol) of the (Z)—N-[2-(diethylamino)ethyl]-2,4-dimethyl-5-[(2-oxo-5-(2-phenylthiazol-4-yl)indolin-3-ylidene)methyl]-1H-pyrrole-3-carboxamide crudely purified product obtained in Production example 1, and then the mixture was heat-stirred at 80° C. PS-TsCl (85 mg, load: 1.97 mmol/g, made by Biotage) was added, and then the reaction mixture was heat-stirred at the same temperature. After 20 minutes, the reaction solution was filtered, and then the product on the filter was washed with dimethylacetamide (7.6 g). After acetonitrile (7.6 g) was added, the mixture was stirred at 60° C. for 1 hour. After acetonitrile (38.1 g) was added for 1 hour, the mixture was cooled to 0° C. over 3 hours. The mixture was stirred at the same temperature for 12 hours, and then the crystal was filtered. The resulting crystal was washed with ethyl acetate (27.0 g) and dried under reduced pressure at 45° C. to yield the titled compound (2.8 g, 5.2 mmol). At that time, the content of the de-ethylated compound was 0.02% and the removal ratio was 92%.

Comparative Example 1

Purification of the Compound Represented by Formula (1)

Purification of (Z)—N-[2-(diethylamino)ethyl]-2,4-dimethyl-5-[(2-oxo-5-(2-phenylthiazol-4-yl) indolin-3-ylidene)methyl]-1H-pyrrole-3-carboxamide Dimethylacetamide (28.3 g) was added to the crystal (3.00 g, 5.6 mmol) of the (Z)—N-[2-(diethylamino)ethyl]-2,4-dimethyl-5-[(2-oxo-5-(2-phenylthiazol-4-yl)indolin-3-ylidene)methyl]-1H-pyrrole-3-carboxamide crudely purified product obtained in Production example 1, and then the mixture was heat-stirred at 80° C. After 20 minutes, the reaction solution was filtered, and then the product on the filter was washed with dimethylacetamide (7.6 g). After acetonitrile (7.6 g) was added, the mixture was stirred at 60° C. for 1 hour. After acetonitrile (38.1 g) was added over 1 hour, the mixture was cooled to 0° C. over 3 hours. The mixture was stirred at the same temperature for 12 hours, and then the crystal was filtered. The resulting crystal was washed with ethyl acetate (27.0 g) and dried under reduced pressure at 45° C. to yield the titled compound (2.8 g, 5.2 mmol). At that time, the content of the de-ethylated compound was 0.29%, and the removal ratio was −21%.

Comparative Example 2

Figure 1:
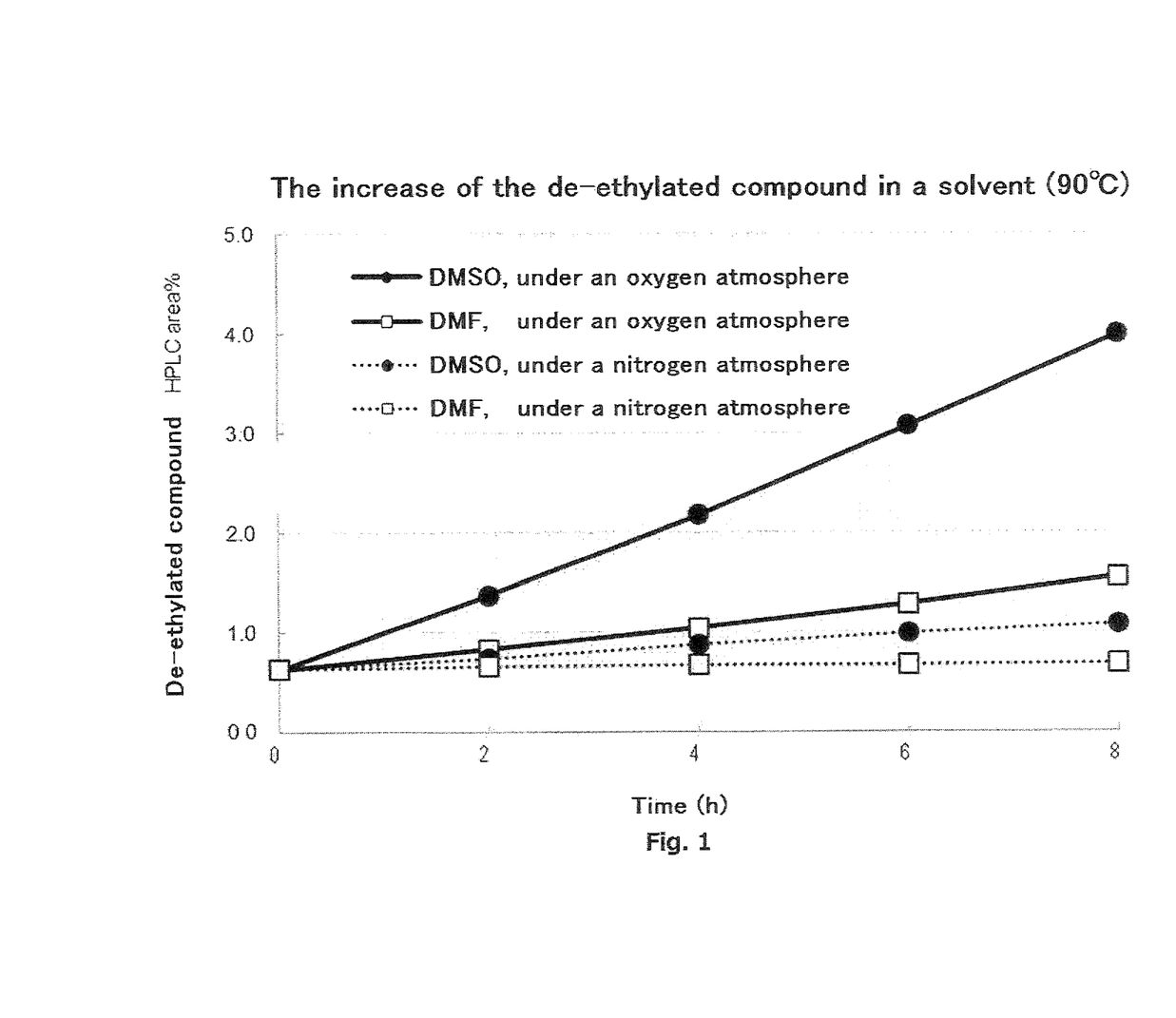
FIG. 1 shows a result of measuring the amount of a compound represented by formula (7) comprised in the production process of a crudely purified product of a compound represented by formula (1), and an experimental result exhibiting the influence of solvents used (DMSO and DMF).

The crudely purified product of Production example 1 was dissolved in dimethyl sulfoxide (DMSO) or dimethylformamide (DMF), and then heat-stirred at 90° C. under an oxygen atmosphere or a nitrogen atmosphere. The reaction solutions were sampled every 2 hours, and then measured by HPLC to investigate the increase or decrease of the de-ethylated compound. The results thereof are shown in FIG. 1.

Comparative Example 3

Ten times by weight of dimethylacetamide (DMA) was added to the crudely purified product of Production example 1, and then the mixture was heated to 80° C. After the crudely purified product was confirmed to have been dissolved, the other solvent shown in the following Table 1 was added dropwise. After cooling to room temperature, filtration and separation of the precipitated crystal gave the purified crystal. The contents and removal ratios of the de-ethylated compound comprised in the purified crystal are shown in Table 1.

TABLE 1

The content of the de-ethylated compound after recrystallization

| Entry | Recrystallization solvent | Purity (HPLC Area %) | Content of the de-ethylated compound (HPLC Area %) | Removal ratio of the de-ethylated compound |
|---|---|---|---|---|
| 0 | Crudely purified product | 99.63 | 0.11 | — |
| 1 | DMA/EtOH 10/20 (wt) | 99.72 | 0.09 | 24% |
| 2 | DMA/MeOH 10/20 (wt) | 99.65 | 0.11 | 5% |
| 3 | DMA/IPA 10/20 (wt) | 99.67 | 0.11 | 7% |
| 4 | DMA/Toluene 10/30 (wt) | 99.60 | 0.09 | 25% |
| 5 | DMA/Acetone 10/26 (wt) | 99.83 | 0.07 | 37% |

As shown in the above Table 1, even though various solvents were used to carry out the recrystallization, the removal ratios of the de-ethylated compound were from 5 to 37%. It was found that the de-ethylated compound comprised in the crudely purified product cannot be efficiently and fully removed. On the other hand, as shown in Example 1, when the purification method of the present invention was used, the removal ratio was 92%. The purification method of the present invention enables efficient purification.

In addition, the results of measuring the purity are shown below.

TABLE 2

| Sample | Production example 1 | Comparative example 1 | Example 1 |
|---|---|---|---|
|  | Crudely purified product | Purified product | Purified product |
| PS-TsCl treatment |  | No | Yes |
| Content of the de-ethylated compound (HPLC area %) | 0.24% | 0.29% | 0.02% |

TABLE 2-continued

|  | Production example 1 | Comparative example 1 | Example 1 |
|---|---|---|---|
| Removal ratio of the de-ethylated compound | — | −21% | 92% |
| Purity of the product (HPLC area %) | 99.59% | 99.35% | 99.80% |

HPLC Condition
1. Sample Solution
    Dissolving solvent: 1% TFA methanol solution
2. HPLC Condition
Column: XBridge Shield RP18 (φ4.6×150 mm I.D, 3.5 μm, Waters)
Column temperature: 40° C.
Mobile Phase A: 0.1% TFA/water
Mobile Phase B: 0.1% TFA/MeCN
Gradient Program:

TABLE 3

| Time (minute) | B (vol %) |
|---|---|
| 0.00 | 20 |
| 5.00 | 40 |
| 10.50 | 90 |
| 13.50 | 90 |
| 13.51 | 20 |
| 15.00 | 20 |

Flow rate: 2.4 mL/min
Detector: uv (300 nm)
Detection range: 1.0 AU/V
Injection volume: 10 μL
Analytical time: 15 min
Washing of a syringe: MeOH/water=7/3

Production Example 2

Production of Another Compound (A Crudely Purified Product)

Production of (Z)—N-[2-(dimethylamino)ethyl]-2,4-dimethyl-5-{[2-oxo-5-(2-phenylthiazol-4-yl)indolin-3-ylidene]methyl}-1H-pyrrole-3-carboxamide (a crudely purified product)

The titled compound can be produced by using the same procedure as Production example 1.
Dimethylformamide is added to 5-(2-chloroacetyl)indolin-2-one and thiobenzamide, and then the mixture is heat-stirred at 80° C. After 4 hours, the mixture is cooled to 60° C., and then N-(2-(dimethylamino)ethyl)-5-formyl-2,4-dimethyl-1H-pyrrole-3-carboxamide dissolved in dimethylformamide, followed by pyrrolidine are added. After 2 hours, acetonitrile is added dropwise over 30 minutes. After stirring at the same temperature for 30 minutes, the mixture is cooled to 20° C. over 3 hours. The precipitated crystal is filtered, and then the crude crystal can be washed with acetonitrile and dried under reduced pressure at 45° C. to yield a crudely purified product of the titled compound.

Example 2

Purification of (Z)—N-[2-(dimethylamino)ethyl]-2,4-dimethyl-5-{[2-oxo-5-(2-phenylthiazol-4-yl)indolin-3-ylidene]methyl}-1H-pyrrole-3-carboxamide The titled compound can be purified by using the same procedure as Example 1.
Dimethylacetamide is added to the crystal of the (Z)—N-[2-(dimethylamino)ethyl]-2,4-dimethyl-5-{[2-oxo-5-(2-phenylthiazol-4-yl)indolin-3-ylidene]methyl}-1H-pyrrole-3-carboxamide crudely purified product obtained in Production example 2, and then the mixture is heat-stirred at 80° C. PS-TsCl (load: 1.97 mmol/g, made by Biotage) is added, and then the reaction mixture is heat-stirred at the same temperature. After 20 minutes, the reaction solution is filtered, and then the product on the filter is washed with dimethylacetamide. After acetonitrile is added, the mixture is stirred at 60° C. for 1 hour. After acetonitrile is added over 1 hour, the mixture is cooled to 0° C. over 3 hours. The mixture is stirred at the same temperature for 12 hours, and then the crystal is filtered. The resulting crystal can be washed with ethyl acetate and dried under reduced pressure at 45° C. to yield the titled compound.

Production Example 3

Production of Another Compound (A Crudely Purified Product)

Production of (Z)—N-[2-(dimethylamino)ethyl]-2,4-dimethyl-5-({2-oxo-5-[2-(pyridin-2-yl)thiazol-4-yl]indolin-3-ylidene}methyl)-1H-pyrrole-3-carboxamide (A Crudely Purified Product)

The titled compound can be produced by using the same procedure as Production example 1.
Dimethylformamide is added to 5-(2-chloroacetyl)indolin-2-one and pyridine-2-carbothioamide, and then the mixture is heat-stirred at 80° C. After 4 hours, the mixture is cooled to 60° C., and then N-(2-(dimethylamino)ethyl)-5-formyl-2,4-dimethyl-1H-pyrrole-3-carboxamide dissolved in dimethylformamide, followed by pyrrolidine are added. After 2 hours, acetonitrile is added dropwise over 30 minutes. After stirring at the same temperature for 30 minutes, the mixture is cooled to 20° C. over 3 hours. The precipitated crystal is filtered, and then the crude crystal can be washed with acetonitrile and dried under reduced pressure at 45° C. to yield a crudely purified product of the titled compound.

Example 3

Purification of (Z)—N-[2-(dimethylamino)ethyl]-2,4-dimethyl-5-({2-oxo-5-[2-(pyridin-2-yl)thiazol-4-yl]indolin-3-ylidene}methyl)-1H-pyrrole-3-carboxamide The titled compound can be purified by using the same procedure as Example 1.
Dimethylacetamide is added to the crystal of the (Z)—N-[2-(dimethylamino)ethyl]-2,4-dimethyl-5-({2-oxo-5-[2-(pyridin-2-yl)thiazol-4-yl]indolin-3-ylidene}methyl)-1H-pyrrole-3-carboxamide crudely purified product obtained in Production example 3, and then the mixture is heat-stirred at 80° C. PS-TsCl (load: 1.97 mmol/g, made by Biotage) is added, and then the reaction mixture is heat-stirred at the same temperature. After 20 minutes, the reaction solution is filtered, and then the product on the filter is washed with dimethylacetamide. After acetonitrile is added, the mixture is stirred at 60° C. for 1 hour. After acetonitrile is added over 1 hour, the mixture is cooled to 0° C. over 3 hours. The mixture is stirred at the same temperature for 12 hours, and then the crystal is filtered. The resulting crystal can be washed with ethyl acetate and dried under reduced pressure at 45° C. to yield the titled compound.

Production Example 4

Production of Another Compound (A Crudely Purified Product)

Production of (Z)—N-[3-(dimethylamino)propyl]-2,4-dimethyl-5-{[2-oxo-5-(2-phenylthiazol-4-yl)indolin-3-ylidene]methyl}-1H-pyrrole-3-carboxamide (A Crudely Purified Product)

The titled compound can be produced by using the same procedure as Production example 1.

Dimethylformamide is added to 5-(2-chloroacetyl)indolin-2-one and thiobenzamide, and then the mixture is heat-stirred at 80° C. After 4 hours, the mixture is cooled to 60° C., and then N-(2-(dimethylamino)propyl)-5-formyl-2,4-dimethyl-1H-pyrrole-3-carboxamide dissolved in dimethylformamide, followed by pyrrolidine are added. After 2 hours, acetonitrile is added dropwise over 30 minutes. After stirring at the same temperature for 30 minutes, the mixture is cooled to 20° C. for 3 hours. The precipitated crystal is filtered, and then the crude crystal can be washed with acetonitrile and dried under reduced pressure at 45° C. to yield a crudely purified product of the titled compound.

Example 4

Purification of (Z)—N-[3-(dimethylamino)propyl]-2,4-dimethyl-5-{[2-oxo-5-(2-phenylthiazol-4-yl)indolin-3-ylidene]methyl}-1H-pyrrole-3-carboxamide The titled compound can be purified by using the same procedure as Example 1.

Dimethylacetamide is added to the crystal of the (Z)—N-[3-(dimethylamino)propyl]-2,4-dimethyl-5-{[2-oxo-5-(2-phenylthiazol-4-yl)indolin-3-ylidene]methyl}-1H-pyrrole-3-carboxamide crudely purified product obtained in Production example 4, and then the mixture is heat-stirred at 80° C. PS-TsCl (load: 1.97 mmol/g, made by Biotage) is added, and then the reaction mixture is heat-stirred at the same temperature. After 20 minutes, the reaction solution is filtered, and then the product on the filter is washed with dimethylacetamide. After acetonitrile is added, the mixture is stirred at 60° C. for 1 hour. After acetonitrile is added over 1 hour, the mixture is cooled to 0° C. over 3 hours. The mixture is stirred at the same temperature for 12 hours, and then the crystal is filtered. The resulting crystal can be washed with ethyl acetate and dried under reduced pressure at 45° C. to yield the titled compound.

Production Example 5

Production of Another Compound (A Crudely Purified Product)

Production of (Z)—N-[2-(di-n-propylamino)ethyl]-2,4-dimethyl-5-{[2-oxo-5-(2-phenylthiazol-4-yl)indolin-3-ylidene]methyl}-1H-pyrrole-3-carboxamide (A Crudely Purified Product)

The titled compound can be produced by using the same procedure as Production example 1.

Dimethylformamide is added to 5-(2-chloroacetyl)indolin-2-one and thiobenzamide, and then the mixture is heat-stirred at 80° C. After 4 hours, the mixture is cooled to 60° C., and then N-(2-(di-n-propylamino)ethyl)-5-formyl-2,4-dimethyl-1H-pyrrole-3-carboxamide dissolved in dimethylformamide, followed by pyrrolidine are added. After 2 hours, acetonitrile is added dropwise over 30 minutes. After stirring at the same temperature for 30 minutes, the mixture is cooled to 20° C. over 3 hours. The precipitated crystal is filtered, and then the crude crystal can be washed with acetonitrile and dried under reduced pressure at 45° C. to yield a crudely purified product of the titled compound.

Example 5

Purification of (Z)—N-[2-(di-n-propylamino)ethyl]-2,4-dimethyl-5-([2-oxo-5-(2-phenylthiazol-4-yl)indolin-3-ylidene]methyl)-1H-pyrrole-3-carboxamide The titled compound can be purified by using the same procedure as Example 1.

Dimethylacetamide is added to the crystal of the (Z)—N-[2-(di-n-propylamino)ethyl]-2,4-dimethyl-5-{[2-oxo-5-(2-phenylthiazol-4-yl)indolin-3-ylidene]methyl}-1H-pyrrole-3-carboxamide crudely purified product obtained in Production example 5, and then the mixture is heat-stirred at 80° C. PS-TsCl (load: 1.97 mmol/g, made by Biotage) is added, and then the reaction mixture is heat-stirred at the same temperature. After 20 minutes, the reaction solution is filtered, and then the product on the filter is washed with dimethylacetamide. After acetonitrile is added, the mixture is stirred at 60° C. for 1 hour. After acetonitrile is added over 1 hour, the mixture is cooled to 0° C. over 3 hours. The mixture is stirred at the same temperature for 12 hours, and then the crystal is filtered. The resulting crystal can be washed with ethyl acetate and dried under reduced pressure at 45° C. to yield the titled compound.

Production Example 6

Production of Another Compound (A Crudely Purified Product)

Production of (Z)—N-[2-(diethylamino)ethyl]-2,4-dimethyl-5-({2-oxo-5-[2-(pyridin-2-yl)thiazol-4-yl]indolin-3-ylidene}methyl)-1H-pyrrole-3-carboxamide (A Crudely Purified Product)

The titled compound can be produced by using the same procedure as Production example 1.

Dimethylformamide is added to 5-(2-chloroacetyl)indolin-2-one and pyridine-2-carbothioamide, and then the mixture is heat-stirred at 80° C. After 4 hours, the mixture is cooled to 60° C., and then N-(2-(diethylamino)ethyl)-5- formyl-2,4-dimethyl-1H-pyrrole-3-carboxamide dissolved in dimethylformamide, followed by pyrrolidine are added. After 2 hours, acetonitrile is added dropwise over 30 minutes. After stirring at the same temperature for 30 minutes, the mixture is cooled to 20° C. over 3 hours. The precipitated crystal is filtered, and then the crude crystal can be washed with acetonitrile and dried under reduced pressure at 45° C. to yield a crudely purified product of the titled compound.

Example 6

Purification of (Z)—N-[2-(diethylamino)ethyl]-2,4-dimethyl-5-({2-oxo-5-[2-(pyridin-2-yl)thiazol-4-yl]indolin-3-ylidene}methyl)-1H-pyrrole-3-carboxamide The titled compound can be purified by using the same procedure as Example 1.

Dimethylacetamide is added to the crystal of the (Z)—N-[2-(diethylamino)ethyl]-2,4-dimethyl-5-({2-oxo-5-[2-(pyridin-2-yl)thiazol-4-yl]indolin-3-ylidene}methyl)-1H-pyrrole-3-carboxamide crudely purified product obtained in Production example 6, and then the mixture is heat-stirred at 80° C. PS-TsCl (load: 1.97 mmol/g, made by Biotage) is added, and then the reaction mixture is heat-stirred at the same temperature. After 20 minutes, the reaction solution is filtered, and then the product on the filter is washed with dimethylacetamide (7.6 g). After acetonitrile is added, the mixture is stirred at 60° C. for 1 hour. After acetonitrile is added over 1 hour, the mixture is cooled to 0° C. over 3 hours. The mixture is stirred at the same temperature for 12 hours, and then the crystal is filtered. The resulting crystal can be washed with ethyl acetate and dried under reduced pressure at 45° C. to yield the titled compound.

Production Example 7

Production of Another Compound (A Crudely Purified Product)

Production of (Z)—N-[2-(di-n-propylamino)ethyl]-2,4-dimethyl-5-((2-oxo-5-[2-(pyridin-2-yl)thiazol-4-yl]indolin-3-ylidene)methyl)-1H-pyrrole-3-carboxamide (A Crudely Purified Product)

The titled compound can be produced by using the same procedure as Production example 1.

Dimethylformamide is added to 5-(2-chloroacetyl)indolin-2-one and pyridine-2-carbothioamide, and then the mixture is heat-stirred at 80° C. After 4 hours, the mixture is cooled to 60° C., and then N-(2-(dipropylamino)ethyl)-5-formyl-2,4-dimethyl-1H-pyrrole-3-carboxamide dissolved in dimethylformamide, followed by pyrrolidine are added. After 2 hours, acetonitrile is added dropwise over 30 minutes. After stirring at the same temperature for 30 minutes, the mixture is cooled to 20° C. over 3 hours. The precipitated crystal is filtered, and then the crude crystal can be washed with acetonitrile and dried under reduced pressure at 45° C. to yield a crudely purified product of the titled compound.

Example 7

Purification of (Z)—N-[2-(di-n-propylamino)ethyl]-2,4-dimethyl-5-({2-oxo-5-[2-(pyridin-2-yl)thiazol-4-yl]indolin-3-ylidene}methyl)-1H-pyrrole-3-carboxamide The titled compound can be purified by using the same procedure as Example 1.

Dimethylacetamide is added to the crystal of the (Z)—N-[2-(di-n-propylamino)ethyl]-2,4-dimethyl-5-((2-oxo-5-[2-(pyridin-2-yl)thiazol-4-yl]indolin-3-ylidene)methyl)-1H-pyrrole-3-carboxamide crudely purified product obtained in Production example 7, and then the mixture is heat-stirred at 80° C. PS-TsCl (load: 1.97 mmol/g, made by Biotage) is added, and then the reaction mixture is heat-stirred at the same temperature. After 20 minutes, the reaction solution is filtered, and then the product on the filter is washed with dimethylacetamide. After acetonitrile is added, the mixture is stirred at 60° C. for 1 hour. After acetonitrile is added for 1 hour, the mixture is cooled to 0° C. over 3 hours. The mixture is stirred at the same temperature for 12 hours, and then the crystal is filtered. The resulting crystal can be washed with ethyl acetate and dried under reduced pressure at 45° C. to yield the titled compound.

As described above, the present invention has been illustrated using the preferable embodiments of the present invention. However, it will be understood that the scope of the present invention should be construed solely on the basis of the claims. It will be understood that the contents of the patents, patent applications, and other documents cited in the present specification should be incorporated by reference to the present specification as if the contents thereof are specifically described herein.

INDUSTRIAL APPLICABILITY

The present invention provides a purification method of a 5-(thiazol-4-yl)indolin-2-one derivative or a pharmaceutically acceptable salt thereof useful as a pharmaceutical product.

The invention claimed is:
1. A purification method of a compound represented by formula (1):

[Chem. 1]

wherein:
$R^1$ and $R^2$ may be identical or different and are each independently an alkyl group or a substituted alkyl group;
$R^3$ is a hydrogen atom, an alkyl group, a substituted alkyl group, a cycloalkyl group, a substituted cycloalkyl group, an aryl group, a substituted aryl group, a heteroaryl group, or a substituted heteroaryl group, or $R^1$ or $R^2$ and $R^3$ are taken together with the nitrogen atom to which they are attached to form a heterocycle or a substituted heterocycle;
$R^4$ and $R^7$ may be identical or different and are each independently a hydrogen atom, an alkyl group, a substituted alkyl group, a cycloalkyl group, a substituted cycloalkyl group, a heterocyclic group, a substituted heterocyclic group, an aryl group, a substituted aryl group, a heteroaryl group, or a substituted heteroaryl group;

R⁵ is a hydrogen atom, an alkyl group, a substituted alkyl group, a cycloalkyl group, a substituted cycloalkyl group, an aryl group, a substituted aryl group, a heteroaryl group, or a substituted heteroaryl group;

R⁶ and R¹² may be identical or different and are each independently a hydrogen atom, a halogen atom, a cyano group, a nitro group, a trifluoromethyl group, a trifluoromethyloxy group, an alkyl group, a substituted alkyl group, a cycloalkyl group, a substituted cycloalkyl group, a heterocyclic group, a substituted heterocyclic group, an aryl group, a substituted aryl group, —OR$^a$, a heteroaryl group, or a substituted heteroaryl group;

R⁸ is a hydrogen atom, an alkyl group, a substituted alkyl group, an alkenyl group, a substituted alkenyl group, an alkynyl group, a substituted alkynyl group, a cycloalkyl group, a substituted cycloalkyl group, a cycloalkenyl group, a substituted cycloalkenyl group, a heterocyclic group, a substituted heterocyclic group, an aryl group, a substituted aryl group, a heteroaryl group, a substituted heteroaryl group, —OR$^a$, —SR$^a$, —S(=O)₂R$^e$, —S(=O)₂OR$^e$, —C(=O)OR$^d$, —C(=O)R$^a$, or —C(=O)NR$^b$R$^c$;

R⁹, R¹⁰, and R¹¹ may be identical or different and are each independently a hydrogen atom, a halogen atom, a cyano group, a nitro group, a trifluoromethyl group, a trifluoromethyloxy group, an alkyl group, a substituted alkyl group, an alkenyl group, a substituted alkenyl group, an alkynyl group, a substituted alkynyl group, a cycloalkyl group, a substituted cycloalkyl group, a cycloalkenyl group, a substituted cycloalkenyl group, a heterocyclic group, a substituted heterocyclic group, an aryl group, a substituted aryl group, a heteroaryl group, a substituted heteroaryl group, —OR$^a$, —SR$^a$, —S(=O)R$^e$, —S(=O)₂R$^e$, —P(=O)₂R$^e$, —S(=O)₂OR$^e$, —P(=O)₂OR$^e$, —NR$^b$R$^c$, —NR$^b$S(=O)₂R$^e$, —NR$^b$P(=O)₂R$^e$, —S(=O)₂NR$^b$R$^c$, —P(=O)₂NR$^b$R$^e$, —C(=O)OR$^e$, —C(=O)R$^a$, —C(=O)NR$^b$R$^c$, —OC(=O)R$^a$, —OC(=O)NR$^b$R$^c$, —NR$^b$C(=O)OR$^e$, —NR$^d$C(=O)NR$^b$R$^c$, —NR$^d$S(=O)₂NR$^b$R$^c$, —NR$^d$P(=O)₂NR$^b$R$^c$, or —NR$^b$C(=O)R$^a$;

R¹³ is a hydrogen atom, an alkyl group, a substituted alkyl group, a cycloalkyl group, a substituted cycloalkyl group, a heterocyclic group, a substituted heterocyclic group, an aryl group, a substituted aryl group, a heteroaryl group, or a substituted heteroaryl group;

n is an integer selected from 2, 3, 4, 5, and 6;

each R$^a$ is independently a hydrogen atom, an alkyl group, a substituted alkyl group, an alkenyl group, a substituted alkenyl group, an alkynyl group, a substituted alkynyl group, a cycloalkyl group, a substituted cycloalkyl group, a cycloalkenyl group, a substituted cycloalkenyl group, a heterocyclic group, a substituted heterocyclic group, an aryl group, or a substituted aryl group;

R$^b$, R$^c$, and R$^d$ may be identical or different and are each independently a hydrogen atom, an alkyl group, a substituted alkyl group, a cycloalkyl group, a substituted cycloalkyl group, a heterocyclic group, a substituted heterocyclic group, an aryl group, or a substituted aryl group, or said R$^b$ and R$^c$ are optionally taken together with the nitrogen atom to which they are attached to form a heterocycle or a substituted heterocycle;

each R$^e$ is independently an alkyl group, a substituted alkyl group, an alkenyl group, a substituted alkenyl group, an alkynyl group, a substituted alkynyl group, a cycloalkyl group, a substituted cycloalkyl group, a cycloalkenyl group, a substituted cycloalkenyl group, a heterocyclic group, a substituted heterocyclic group, an aryl group, or a substituted aryl group; and the wavy line represents either cis or trans, or a geometrical isomer thereof, or a mixture thereof, or a pharmaceutically acceptable salt thereof, wherein the method comprises a step of removing a compound represented by the following formula (7):

[Chem. 2]

(7)

wherein n, R³, R⁴, R⁵, R⁶, R⁷, R⁸, R⁹, R¹⁰, R¹¹, R¹², R¹³, and the wavy line are defined the same as in the compound represented by formula (1), and R¹⁴ is an alkyl group or a substituted alkyl group, or R¹⁴ and R³ are taken together with the nitrogen atom to which they are attached to form a heterocycle or a substituted heterocycle, or a geometrical isomer thereof, or a mixture thereof, or a pharmaceutically acceptable salt thereof by using a solid-phase supported adsorbent in the presence of a purification solvent.

2. The purification method according to claim 1, wherein:

R¹ and R² may be identical or different and are each independently a C$_{1-6}$alkyl group, R³, R⁴, R⁵, R⁶, R⁷, R⁸, R⁹, R¹⁰, R¹¹, R¹², and R¹³ may be identical or different and are each independently a hydrogen atom, a C$_{1-6}$alkyl group, a substituted C$_{1-6}$alkyl group, a C$_{3-6}$cycloalkyl group, a substituted C$_{3-6}$cycloalkyl group, a C$_{6-10}$aryl group, a substituted C$_{6-10}$aryl group, a 5- to 10-membered heteroaryl group, or a 5- to 10-membered substituted heteroaryl group, and R¹⁴ is a C$_{1-6}$alkyl group; or R¹ or R² and R³ are taken together with the nitrogen atom to which they are attached to form a 6- to 10-membered heterocycle or substituted heterocycle, R⁴, R⁵, R⁶, R⁷, R⁸, R⁹, R¹⁰, R¹¹, R¹², and R¹³ may be identical or different and are each independently a hydrogen atom, a C$_{1-6}$alkyl group, a substituted C$_{1-6}$alkyl group, a C$_{3-6}$cycloalkyl group, a substituted C$_{3-6}$cycloalkyl group, a C$_{6-10}$aryl group, a substituted C$_{6-10}$aryl group, a 5- to 10-membered heteroaryl group, or a 5- to 10-membered substituted heteroaryl group, and $R^{14}$ and $R^3$ are taken together with the nitrogen atom to which they are attached to form a 6- to 10-membered heterocycle or substituted heterocycle.

3. The purification method according to claim 1, wherein $R^1$ and $R^2$ may be identical or different and are each independently a $C_{1-6}$alkyl group, $R^3$, $R^4$, $R^5$, $R^6$, $R^7$, $R^8$, $R^9$, $R^{10}$, $R^{11}$, $R^{12}$, and $R^{13}$ may be identical or different and are each independently a hydrogen atom, a $C_{1-6}$alkyl group, a $C_{6-10}$aryl group, or a 5- to 10-membered heteroaryl group, and $R^{14}$ is a $C_{1-6}$alkyl group.

4. The purification method according to claim 1, wherein the purification solvent is an oxidation-non-inducing solvent.

5. The purification method according to claim 1, wherein the purification is carried out under a nitrogen atmosphere.

6. The purification method according to claim 1, wherein the adsorption portion of the solid-phase supported adsorbent is toluenesulfonyl chloride, sulfonic acid, toluenesulfonic acid, isocyanate, or carbodiimide.

7. The purification method according to claim 6, wherein the adsorption portion of the solid-phase supported adsorbent is toluenesulfonyl chloride.

8. The purification method according to claim 1, wherein the solid-phase portion of the solid-phase supported adsorbent is polystyrene.

9. The purification method according to claim 1, wherein $R^1$ and $R^2$ may be identical or different and are each independently a $C_{1-3}$alkyl group.

10. The purification method according to claim 9, wherein $R^1$ and $R^2$ are both ethyl groups.

11. The purification method according to claim 1, wherein $R^{13}$ is an aryl group.

12. The purification method according to claim 11, wherein $R^{13}$ is a phenyl group.

13. The purification method according to claim 1, wherein $R^4$ and $R^6$ may be identical or different and are each independently a $C_{1-6}$alkyl group.

14. The purification method according to claim 13, wherein $R^4$ and $R^6$ may be identical or different and are each independently a $C_{1-3}$alkyl group.

15. The purification method according to claim 1, wherein $R^3$ and $R^5$ are both hydrogen atoms.

16. The purification method according to claim 1, wherein $R^7$, $R^8$, $R^9$, $R^{10}$, $R^{11}$, and $R^{12}$ are all hydrogen atoms.

17. The purification method according to claim 1, wherein the method comprises a step of reacting a crudely purified product comprising the compound represented by formula (1) with the solid-phase supported adsorbent, then separating the solid-phase supported adsorbent by filtration, and further adding a crystallization solvent to crystallize the compound represented by formula (1).

18. The purification method according to claim 1, wherein the proportion of the compound represented by formula (7) in a crudely purified product of the compound represented by formula (1) is 0.1% by weight or less.

19. The purification method according to claim 18, wherein the proportion of the compound represented by formula (7) in the crudely purified product of the compound represented by formula (1) is 0.05% by weight or less.

20. The purification method according to claim 1, wherein the removal ratio of the compound represented by formula (7) is 80% or greater.

* * * * *